US012568983B2

(12) United States Patent
Fang et al.

(10) Patent No.: US 12,568,983 B2
(45) Date of Patent: Mar. 10, 2026

(54) STREPTOCOCCUS THERMOPHILUS PRODUCING γ-AMINOBUTYRIC ACID AND APPLICATION THEREOF

(71) Applicant: WECARE PROBIOTICS CO., LTD., Jiangsu (CN)

(72) Inventors: Shuguang Fang, Jiangsu (CN); Xiaojuan Guo, Jiangsu (CN); Yanfeng Wu, Jiangsu (CN); Xin Wang, Jiangsu (CN); Jianguo Zhu, Jiangsu (CN)

(73) Assignee: WECARE PROBIOTICS CO., LTD., Jiangsu (CN)

( * ) Notice: Subject to any disclaimer, the term of this patent is extended or adjusted under 35 U.S.C. 154(b) by 129 days.

(21) Appl. No.: 18/009,460

(22) PCT Filed: Mar. 17, 2021

(86) PCT No.: PCT/CN2021/081211

§ 371 (c)(1),
(2) Date: Dec. 9, 2022

(87) PCT Pub. No.: WO2022/193163

PCT Pub. Date: Sep. 22, 2022

(65) Prior Publication Data

US 2023/0413837 A1 Dec. 28, 2023

(51) Int. Cl.
*A23C 9/123* (2006.01)
*A23C 9/13* (2006.01)
(Continued)

(52) U.S. Cl.
CPC .......... *A23C 9/1238* (2013.01); *A23C 9/1234* (2013.01); *A23C 9/1307* (2013.01);
(Continued)

(58) Field of Classification Search
CPC ... A23C 9/1238; A23C 9/1234; A23C 9/1307; A23C 9/137; A23C 2220/208;
(Continued)

(56) References Cited

FOREIGN PATENT DOCUMENTS

| CN | 103155977 A | 6/2013 | |
| CN | 104293699 A * | 1/2015 | .......... A23C 9/1238 |

(Continued)

OTHER PUBLICATIONS

Translation of CN-104293699-A (Year: 2015).*
Hu, et al., "Genome Analysis and Physiological Characterization of Four *Streptococcus thermophilus* Strains Isolated From Chinese Traditional Fermented Milk" Front. Microbiol. (2020) 11:184.
(Continued)

*Primary Examiner* — Brent T O'Hern
(74) *Attorney, Agent, or Firm* — Robert C. Netter, Jr.; Dann, Dorfman, Herrell & Skillman

(57) ABSTRACT

Provided are *Streptococcus thermophilus* for producing γ-aminobutyric acid and an application thereof. The *Streptococcus thermophilus* for producing γ-aminobutyric acid is named *Streptococcus thermophilus* ST 36 and is preserved in the Institute of Microbiology of the Chinese Academy of Sciences, the preservation number being CGMCC NO. 20676, and the preservation date being 18 Sep. 2020. Also provided are a screening method for *Streptococcus thermophilus* for producing γ-aminobutyric acid, a preparation method for a dairy product containing γ-aminobutyric acid, and a dairy product containing γ-aminobutyric acid prepared by using the preparation method. The *Streptococcus thermophilus* for producing γ-aminobutyric acid has strong γ-aminobutyric acid synthesis capability and short fermentation time, and the prepared dairy product contains rich γ-aminobutyric acid.

10 Claims, 2 Drawing Sheets

Specification includes a Sequence Listing.

(51) Int. Cl.

| | | |
|---|---|---|
| *A23C 9/137* | (2006.01) | |
| *C12N 1/205* | (2026.01) | |
| *C12R 1/46* | (2006.01) | |

(52) U.S. Cl.
CPC .............. *A23C 9/137* (2013.01); *C12N 1/205* (2021.05); *A23C 2220/208* (2013.01); *A23V 2400/123* (2023.08); *A23V 2400/125* (2023.08); *A23V 2400/249* (2023.08); *C12R 2001/46* (2021.05)

(58) Field of Classification Search
CPC ............... C12N 1/205; C12R 2001/46; A23V 2400/123; A23V 2400/249; A23V 2400/125
USPC .......................................................... 426/43
See application file for complete search history.

(56) References Cited

FOREIGN PATENT DOCUMENTS

| | | | |
|---|---|---|---|
| CN | 107937311 | A | 4/2018 |
| CN | 109486727 | A | 3/2019 |
| CN | 110218675 | A | 9/2019 |
| CN | 110747145 | A | 2/2020 |
| KR | 1020100012743 | A | 2/2010 |

OTHER PUBLICATIONS

Brasca, et al., "Proteolytic activity and production of gamma-aminobutyric acid by *Streptococcus thermophilus* cultivated in microfiltered pasteurized milk" J. Agric. Food Chem. (2016) 64(45):8604-8614.
PCT/CN2021/081211, International Search Report, 2021.
CN 202180001791.8, Official Action, 2022.

* cited by examiner

SEQUENCE LISTING

```
<160> NUMBER OF SEQ ID NOS: 1

<210> SEQ ID NO 1
<211> LENGTH: 1484
<212> TYPE: DNA
<213> ORGANISM: Streptococcus thermophilus

<400> SEQUENCE: 1
gctcaggacg aacgctggcg gcgtgcctaa tacatgcaag tagaacgctg aagagaggag      60
cttgctcttc ttggatgagt tgcgaacggg tgagtaacgc gtaggtaacc tgccttgtag     120 cggggggataa ctattggaaa cgatagctaa taccgcataa caatggatga cacatgtcat     180
ttatttgaaa ggggcaattg ctccactaca agatggacct gcgttgtatt agctagtagg     240
tgaggtaatg gctcacctag gcgacgatac atagccgacc tgagagggtg atcggccaca     300
ctgggactga gacacggccc agactcctac gggaggcagc agtagggaat cttcggcaat     360
gggggcaacc ctgaccgagc aacgccgcgt gagtgaagaa ggttttcgga tcgtaaagct     420
ctgttgtaag tcaagaacgg gtgtgagagt ggaaagttca cactgtgacg gtagcttacc     480
agaaagggac ggctaactac gtgccagcag ccgcggtaat acgtaggtcc cgagcgttgt     540
ccggatttat tgggcgtaaa gcgagcgcag gcggtttgat aagtctgaag ttaaaggctg     600
tggctcaacc atagttcgct ttggaaactg tcaaacttga gtgcagaagg ggagagtgga     660
attccatgtg tagcggtgaa atgcgtagat atatggagga acaccggtgg cgaaagcggc     720
tctctggtct gtaactgacg ctgaggctcg aaagcgtggg gagcgaacag gattagatac     780
```

-continued

```
cctggtagtc cacgccgtaa acgatgagtg ctaggtgttg gatcctttcc gggattcagt      840
gccgcagcta acgcattaag cactccgcct ggggagtacg accgcaaggt tgaaactcaa      900
aggaattgac gggggcccgc acaagcggtg gagcatgtgg tttaattcga agcaacgcga      960
agaaccttac caggtcttga catcccgatg ctatttctag agatagaaag ttacttcggt     1020
acatcggtga caggtggtgc atggttgtcg tcagctcgtg tcgtgagatg ttgggttaag     1080
tcccgcaacg agcgcaaccc ctattgttag ttgccatcat tcagttgggc actctagcga     1140
gactgccggt aataaaccgg aggaaggtgg ggatgacgtc aaatcatcat gccccttatg     1200
acctgggcta cacacgtgct acaatggttg gtacaacgag ttgcgagtcg gtgacggcga     1260
gctaatctct taaagccaat ctcagttcgg attgtaggct gcaactcgcc tacatgaagt     1320
cggaatcgct agtaatcgcg gatcagcacg ccgcggtgaa tacgttcccg ggccttgtac     1380
acaccgcccg tcacaccacg agagtttgta acacccgaag tcggtgaggt aaccttttgg     1440
agccagccgc ctaaggtggg acagatgatt ggggtgaagt cgta                      1484
```

STREPTOCOCCUS THERMOPHILUS PRODUCING γ-AMINOBUTYRIC ACID AND APPLICATION THEREOF

This application is a § 371 application of PCT/CN2021/081211, filed Mar. 17, 2021. The foregoing application is incorporated by reference herein.

TECHNICAL FIELD

The present application belongs to the technical field of microbial fermentation engineering and, in particular, relates to a γ-aminobutyric acid-producing *Streptococcus thermophilus* and a use thereof.

BACKGROUND

γ-Aminobutyric acid (GABA) is a natural four-carbon, non-protein amino acid found widely in vertebrates, plants and microorganisms. GABA has important physiological functions such as anti-aging, blood pressure regulation, and anti-anxiety and has good efficacy in the treatment of mental disorders, sleep improvement, and other aspects.

The content of γ-aminobutyric acid in natural foods is relatively low, and γ-aminobutyric acid ingested from foods cannot satisfy the basic daily requirement of a human body. Current methods for preparing γ-aminobutyric acid mainly include chemical synthesis method, plant enrichment method, and microbial fermentation method. Due to the disadvantages of severe reaction conditions, relatively large toxicity of raw materials, low safety, and a high cost, the preparation of γ-aminobutyric acid by a conventional chemical synthesis method is not suitable for the preparation of γ-aminobutyric acid at a pharmaceutical and food safety grade. The plant enrichment method requires a large quantity of raw materials for production and a relatively high production cost and its yield is often not ideal. The microbial fermentation method is to prepare and produce γ-aminobutyric acid by screening excellent, stable, non-toxic, and harmless strains and using growth and reproduction processes of fungi. In contrast, the preparation of γ-aminobutyric acid by the microbial fermentation method requires mild reaction conditions and has a relatively high safety coefficient and thus gradually becomes the main method for preparing γ-aminobutyric acid at the pharmaceutical and food safety grade. CN110747145A discloses a *lactobacillus* highly producing γ-aminobutyric acid, an isolation and culture method therefor, and a use thereof. A strain of the *lactobacillus* for producing γ-aminobutyric acid is screened from fermented pickled products through the screening, primary screening, and re-screening on pure-bred colonies, and the strain can be used for preparing related products such as fermented beverages. However, the *lactobacillus* has a relatively weak γ-aminobutyric acid synthesis ability and only functions in a range of 0.67-0.68 g/L, the yield is relatively low, and the fermentation time is relatively long.

At present, most strains for synthesizing γ-aminobutyric acid are lactobacilli, and there are problems of a long fermentation period and a relatively weak γ-aminobutyric acid synthesis ability. Therefore, how to provide a strain which has a strong γ-aminobutyric acid synthesis ability and a short fermentation period to promote the industrial production of γ-aminobutyric acid is an urgent problem to be solved.

SUMMARY

The present application provides a γ-aminobutyric acid-producing *Streptococcus thermophilus* and a use thereof.

*Streptococcus thermophilus* has a strong γ-aminobutyric acid synthesis ability and a short fermentation period, can rapidly produce a large amount of fermentation products, and is applied to preparation of related products with an extremely high application value.

In a first aspect, the present application provides a γ-aminobutyric acid-producing *Streptococcus thermophilus*, which is named *Streptococcus thermophilus* ST36 and deposited in the China General Microbiological Culture Collection Center on Sep. 18, 2020, with deposit No. CGMCC NO.20676.

In the present application, the γ-aminobutyric acid-producing *Streptococcus thermophilus* has the advantages of synthesis of a large amount of γ-aminobutyric acid and a short fermentation time and overcomes the problems of a long fermentation period and synthesis of a small amount of γ-aminobutyric acid of most lactobacilli at present. In addition, when *Streptococcus thermophilus* is applied to the preparation of a fermented food, the fermented food prepared can improve an intestinal microenvironment and regulate the balance of flora. *Streptococcus thermophilus* has higher safety and a higher application value compared with *Escherichia coli* as a fermentation strain.

In a second aspect, the present application provides a method for screening the γ-aminobutyric acid-producing *Streptococcus thermophilus* in the first aspect. The method includes screening single colonies by a solid medium, primary screening by thin-layer chromatography, and re-screening by high-performance liquid chromatography to obtain the γ-aminobutyric acid-producing *Streptococcus thermophilus*.

In the present application, the single colonies are screened to ensure that the finally screened strain is a monoclone, which is essential for maintaining the stability of a strain; the thin-layer chromatography can rapidly isolate γ-aminobutyric acid and react with a chromogenic reagent for qualitative detection to primarily screen a strain capable of producing γ-aminobutyric acid; γ-aminobutyric acid can be quantitatively reacted with ortho-phthalaldehyde to produce an isoindole derivative having fluorescence and an ultraviolet absorption capacity so that a high-performance liquid chromatograph with an ultraviolet detector can be used for quantitative detection to determine the γ-aminobutyric acid synthesis abilities of different strains and screen a strain having a strongest synthesis ability.

Preferably, the solid medium includes a de Man, Rogosa, Sharpe (MRS) solid medium containing bromocresol purple.

Preferably, the screening single colonies includes screening from a milk tofu sample diluent.

In the present application, the milk tofu is a food obtained by coagulation and fermentation of cow milk, goat milk and horse milk.

Preferably, a step of cryopreservation is further comprised after the screening single colonies by a solid medium.

Preferably, the cryopreservation is conducted at a temperature of −75° C. to −85° C., which may be, for example, −75° C., −76° C., −77° C., −78° C., −79° C., −80° C., −81° C., −82° C., −83° C., −84° C., or −85° C., preferably −80° C.

Preferably, the screening single colonies includes specific steps of coating a milk tofu sample diluent on a surface of an MRS solid medium containing bromocresol purple, and screening yellow single colonies; and repeatedly streaking and culturing the obtained single colonies to obtain pure colonies, and conducting cryopreservation at −75° C. to −85° C.

Preferably, the primary screening by thin-layer chromatography includes: activating cryopreserved bacteria, inoculating the activated bacteria in a liquid medium, conducting static culture, subjecting a culture supernatant to chromatographic identification, and primarily determining an ability of a strain to produce γ-aminobutyric acid to obtain a primarily screened strain.

Preferably, a step of the activating includes inoculating the cryopreserved bacteria in an MRS liquid medium and activating and culturing the cryopreserved bacteria twice.

Preferably, the activating and culturing is conducted at a temperature of 36.5° C. to 37.5° C., which may be, for example, 36.5° C., 36.6° C., 36.7° C., 36.8° C., 36.9° C., 37° C., 37.1° C., 37.2° C., 37.3° C., 37.4° C., or 37.5° C., preferably 37° C.

Preferably, the activating and culturing is conducted for 16-18 h, which may be, for example, 16 h, 16.5 h, 17 h, 17.5 h, or 18 h.

Preferably, a liquid medium for the static culture is an MRS liquid medium containing 0.8%4.2% L-sodium glutamate, where a mass fraction of L-sodium glutamate may be, for example, 0.8%, 1%, 1.1%, or 1.2%.

Preferably, an inoculation volume for the static culture is 1%-4%, which may be, for example, 1%, 1.5%, 2%, 2.5%, 3%, 3.5%, or 4%.

Preferably, the static culture is conducted at a temperature of 36.5° C. to 37.5° C., which may be, for example, 36.5° C., 36.6° C., 36.7° C., 36.8° C., 36.9° C., 37° C., 37.1° C., 37.2° C., 37.3° C., 37.4° C., or 37.5° C., preferably 37° C.

Preferably, the static culture is conducted for 24-48 h, which may be, for example, 24 h, 26 h, 28 h, 30 h, 32 h, 34 h, 36 h, 38 h, 40 h, 42 h, 44 h, 46 h, or 48 h.

Preferably, the culture supernatant is obtained by centrifugation.

Preferably, the primary screening by thin-layer chromatography includes specific steps of inoculating the cryopreserved bacteria in the MRS liquid medium, activating and culturing the cryopreserved bacteria at 36.5° C. to 37.5° C. for 16-18 h, inoculating the activated bacteria in the MRS liquid medium containing 0.8%4.2% L-sodium glutamate at an inoculation volume of 1%-4%, conducting the static culture at 36.5° C. to 37.5° C. for 24-48 h, subjecting the culture supernatant obtained by the centrifugation to chromatography, and primarily determining the ability of the strain to produce γ-aminobutyric acid to obtain the primarily screened strain.

Preferably, the re-screening by high-performance liquid chromatography includes: activating and culturing a primarily screened strain, conducting static culture, taking a culture fermentation broth, and detecting a content of γ-aminobutyric acid in the culture fermentation broth by an ortho-phthalaldehyde pre-column derivatization-ultraviolet detection method to obtain a re-screened strain.

Preferably, a medium for the activating and culturing includes an MRS liquid medium.

Preferably, the activating and culturing is conducted at a temperature of 36.5° C. to 37.5° C., which may be, for example, 36.5° C., 36.6° C., 36.7° C., 36.8° C., 36.9° C., 37° C., 37.1° C., 37.2° C., 37.3° C., 37.4° C., or 37.5° C., preferably 37° C.

Preferably, the activating and culturing is conducted for 16-18 h, which may be, for example, 16 h, 16.5 h, 17 h, 17.5 h, or 18 h.

Preferably, a medium for the static culture includes an MRS liquid medium containing L-sodium glutamate.

Preferably, the static culture is conducted at a temperature of 36.5° C. to 37.5° C., which may be, for example, 36.5° C., 36.6° C., 36.7° C., 36.8° C., 36.9° C., 37° C., 37.1° C., 37.2° C., 37.3° C., 37.4° C., or 37.5° C., preferably 37° C.

Preferably, the static culture is conducted for 24-48 h, which may be, for example, 24 h, 26 h, 28 h, 30 h, 32 h, 34 h, 36 h, 38 h, 40 h, 42 h, 44 h, 46 h, or 48 h.

Preferably, the culture fermentation broth is obtained by centrifugation.

Preferably, the re-screening by high-performance liquid chromatography includes specific steps of activating and culturing the primarily screened strain in the MRS liquid medium at 36.5° C. to 37.5° C. for 16-18 h, inoculating the strain in the MRS liquid medium containing L-sodium glutamate, conducting the static culture at 36.5° C. to 37.5° C. for 24-48 h, obtaining the culture fermentation broth by the centrifugation, and detecting the content of γ-aminobutyric acid in the culture fermentation broth by the ortho-phthalaldehyde pre-column derivatization-ultraviolet detection method to obtain the re-screened strain.

As a preferred technical solution, the method for screening γ-aminobutyric acid-producing *Streptococcus thermophilus* in the present application specifically includes the following steps:

(1) coating a milk tofu sample diluent on a surface of an MRS solid medium containing bromocresol purple, and screening yellow single colonies; and repeatedly streaking and culturing the obtained single colonies to obtain pure colonies, and conducting cryopreservation at −75° C. to −85° C.;

(2) inoculating cryopreserved bacteria in an MRS liquid medium, activating and culturing the cryopreserved bacteria at 36.5° C. to 37.5° C. for 16-18 h, inoculating the activated bacteria in an MRS liquid medium containing 0.8%-1.2% L-sodium glutamate at an inoculation volume of 1%-4%, conducting static culture at 36.5° C. to 37.5° C. for 24-48 h, subjecting a culture supernatant obtained by centrifugation to chromatography, and primarily determining an ability of a strain to produce γ-aminobutyric acid to obtain a primarily screened strain;

(3) activating and culturing the primarily screened strain in an MRS liquid medium at 36.5° C. to 37.5° C. for 16-18 h, inoculating the strain in an MRS liquid medium containing L-sodium glutamate, conducting static culture at 36.5° C. to 37.5° C. for 24-48 h, obtaining a culture fermentation broth by centrifugation, and detecting a content of γ-aminobutyric acid in the culture fermentation broth by an ortho-phthalaldehyde pre-column derivatization-ultraviolet detection method to obtain a re-screened strain.

In a third aspect, the present application provides a use of γ-aminobutyric acid-producing *Streptococcus thermophilus* in the first aspect for preparing a γ-aminobutyric acid-containing dairy product.

In the present application, the γ-aminobutyric acid-producing *Streptococcus thermophilus* has the advantages of a high yield and a short time consumed and is applied to the preparation of the related dairy product. The product has a conventional fermentation product of *Streptococcus thermophilus* and is rich in γ-aminobutyric acid and has intestinal flora regulation, blood pressure regulation, emotion mitigation, lipid metabolism improvement, and anti-aging effects and an extremely high application value.

In a fourth aspect, the present application provides a preparation method of a γ-aminobutyric acid-containing dairy product. The preparation method includes: activating a strain, preparing a fermentation agent, preparing a fermentation base, and conducting inoculation and fermentation.

In the present application, the preparation method is simple and convenient to operate, the fermentation following strain activation can ensure a more sufficient fermentation process, and the product has a higher content of γ-aminobutyric acid, improved appearance, smell, and mouthfeel, better flavor, and a higher nutritional value and is beneficial for physical health.

Preferably, the activating a strain includes inoculating γ-aminobutyric acid-producing *Streptococcus thermophilus* in an MRS liquid medium and culturing the strain at 37° C. to 45° C. for 12-24 h, where the culture temperature may be, for example, 37° C., 38° C., 39° C., 40° C., 41° C., 42° C., 43° C., 44° C., or 45° C., and the culture time may be, for example, 12 h, 13 h, 14 h, h, 16 h, 17 h, 18 h, 19 h, 20 h, 21 h, 22 h, 23 h, or 24 h.

Preferably, the activating a strain further includes a step of inoculating *Lactobacillus bulgaricus* and/or *Lactobacillus casei* in an MRS liquid medium separately.

Preferably, the preparing a fermentation agent includes inoculating and culturing the activated strain in a sterilized skim milk medium to obtain the fermentation agent.

Preferably, the inoculating is conducted at a volume of 2%-5%, which may be, for example, 2%, 2.5%, 3%, 3.5%, 4%, 4.5%, or 5%.

Preferably, the sterilization is conducted at a temperature of 110° C. to 120° C., which may be, for example, 110° C., 111° C., 112° C., 113° C., 114° C., 115° C., 116° C., 117° C., 118° C., 119° C., or 120° C.

Preferably, the sterilization is conducted for 10 min to 20 min, which may be, for example, 10 min, 11 min, 12 min, 13 min, 14 min, 15 min, 16 min, 17 min, 18 min, 19 min, or 20 min.

Preferably, a mass fraction of skim milk powder in the skim milk medium is 10%-15%, which may be, for example, 10%, 10.5%, 11%, 11.5%, 12%, 12.5%, 13%, 13.5%, 14%, 14.5%, or 15%, preferably 12%.

Preferably, the culturing is conducted at a temperature of 37° C. to 43° C., which may be, for example, 37° C., 38° C., 39° C., 40° C., 41° C., 42° C., or 43° C.

Preferably, the culturing is conducted for 16-24 h, which may be, for example, 16 h, 17 h, 18 h, 19 h, 20 h, 21 h, 22 h, 23 h, or 24 h.

Preferably, a raw material of the fermentation base includes any one of raw milk, whole milk powder, white sugar, sodium glutamate, glucose, light cream, a stabilizer, whey protein powder, or a thickening agent or a combination of at least two selected therefrom, which may be, for example, a combination of raw milk or whole milk powder with white sugar.

Preferably, the preparing a fermentation base includes mixing raw materials, hydration, homogenization, and sterilization to obtain the fermentation base.

Preferably, the hydration is conducted at a temperature of 40° C. to 50° C., which may be, for example, 40° C., 41° C., 42° C., 43° C., 44° C., 45° C., 46° C., 47° C., 48° C., 49° C., or 50° C.

Preferably, the hydration is conducted for 20-40 min, which may be, for example, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, or 40 min.

Preferably, the homogenization is conducted at a temperature of 60° C. to 70° C., which may be, for example, 60° C., 61° C., 62° C., 63° C., 64° C., 65° C., 66° C., 67° C., 68° C., 69° C., or 70° C.

Preferably, the homogenization is conducted under a pressure of 10-20 MPa, which may be, for example, 10 MPa, 11 MPa, 12 MPa, 13 MPa, 14 MPa, 15 MPa, 16 MPa, 17 MPa, 18 MPa, 19 MPa, or 20 MPa.

Preferably, the sterilization is conducted by pasteurization, where the pasteurization is conducted at a temperature of 80° C. to 90° C. for 15-30 min. The temperature may be, for example, 80° C., 81° C., 82° C., 83° C., 84° C., 85° C., 86° C., 87° C., 88° C., 89° C., or 90° C., and the time may be, for example, 15 min, 16 min, 17 min, 18 min, 19 min, 20 min, 21 min, 22 min, 23 min, 24 min, 25 min, 26 min, 27 min, 28 min, 29 min, or 30 min.

Preferably, the sterilization is followed by a step of cooling to 40° C. to 45° C., where the temperature may be, for example, 40° C., 41° C., 42° C., 43° C., 44° C., or 45° C.

Preferably, the cooling includes cooling by circulating water.

Preferably, an inoculation volume of the fermentation agent during the inoculation and fermentation is 1.5%-6%, which may be, for example, 1.5%, 2%, 2.5%, 3%, 3.5%, 4%, 4.5%, 5%, 5.5%, or 6%.

Preferably, the inoculation and fermentation is conducted at a temperature of 37° C. to 43° C., which may be, for example, 37° C., 38° C., 39° C., 40° C., 41° C., 42° C., or 43° C.

Preferably, the inoculation and fermentation is conducted for 24-48 h, which may be, for example, 24 h, 26 h, 28 h, 30 h, 32 h, 34 h, 36 h, 38 h, 40 h, 42 h, 44 h, 46 h, or 48 h.

Preferably, the inoculation and fermentation further includes a step of cooling to 0° C. to 6° C., where the temperature may be, for example, 0° C., 0.5° C., 1° C., 1.5° C., 2° C., 2.5° C., 3° C., 3.5° C., 4° C., 4.5° C., 5° C., 5.5° C., or 6° C.

Preferably, a step of post-maturation is further included after the cooling.

Preferably, the preparation method further includes a step of secondary dosing.

Preferably, the secondary dosing includes steps of formulating a solvent, adding a fermentation product, then determining a constant volume, adjusting an acid condition, homogenizing, and sterilizing.

Preferably, the solvent includes a thickening agent, white sugar, and water.

Preferably, the thickening agent includes pectin and/or soy polysaccharide.

Preferably, a mass ratio of the thickening agent to white sugar is 1:(20-25), which may be, for example, 1:20, 1:21, 1:22, 1:23, 1:24, or 1:25, preferably 1:22.

Preferably, the solvent is formulated at 60° C. to 75° C., where the temperature may be, for example, 60° C., 61° C., 62° C., 63° C., 64° C., 65° C., 66° C., 67° C., 68° C., 69° C., 70° C., 71° C., 72° C., 73° C., 74° C., or 75° C.

Preferably, the formulating includes steps of mixing the thickening agent with white sugar at a mass ratio of 1:(4-6), adding water, stirring, and adding the remaining white sugar, where the mass ratio may be, for example, 1:4, 1:4.5, 1:5, 1:5.5, or 1:6.

Preferably, the fermentation product is added at a temperature of 20° C. to 30° C., which may be, for example, 20° C., 21° C., 22° C., 23° C., 24° C., 25° C., 26° C., 27° C., 28° C., 29° C., or 30° C.

As a preferred technical solution, the preparation method of a γ-aminobutyric acid-containing dairy product in the present application specifically includes the following steps:

(1) inoculating γ-aminobutyric acid-producing *Streptococcus thermophilus* and *Lactobacillus bulgaricus* and/or *Lactobacillus casei* in an MRS liquid medium separately and culturing a strain at 37° C. to 45° C. for 12-24 h to activate the strain;

(2) inoculating the activated strain at an inoculation volume of 2%-5% in a skim milk medium having a mass fraction of 10%-15% and sterilized at 110° C. to 120° C. for 10-20 min and culturing the activated strain at 37° C. to 43° C. for 16-24 h to obtain a fermentation agent;

(3) mixing raw materials of a fermentation base, conducting hydration at 40° C. to 50° C. for min, conducting homogenization at 60° C. to 70° C. under 10-20 MPa, conducting pasteurization at 80° C. to 90° C. for 15-30 min, and cooling by circulating water to 40° C. to ° C. to obtain the fermentation base;

(4) inoculating the fermentation agent to the fermentation base at a volume of 1.5%-6%, conducting inoculation and fermentation at 37° C. to 43° C. for 24-48 h, cooling to 0° C. to 6° C., and conducting post-maturation to obtain a fermentation product;

(5) formulating a thickening agent and white sugar with a mass ratio of 1:(20-25) at 60° C. to ° C., cooling to 20° C. to 30° C., adding the fermentation product, then determining a constant volume, adjusting an acid condition, homogenizing, and sterilizing to obtain the γ-aminobutyric acid-containing dairy product.

In a fifth aspect, the present application provides a γ-aminobutyric acid-containing dairy product prepared by the preparation method in the fourth aspect.

In the present application, the dairy product prepared by the preparation method in the fourth aspect is rich in protein, γ-aminobutyric acid, and vitamins and rich in nutrition and has anti-aging, blood pressure regulation, anti-anxiety, and sleep improvement effects. The dairy product is fine in taste and excellent in flavor.

Preferably, the dairy product includes any one of fermented milk, a lactic acid bacteria beverage, or a brown lactic acid bacteria beverage.

Compared with the existing art, the present application has the beneficial effects below.

(1) In the present application, a strain of *Streptococcus thermophilus* ST36 producing γ-aminobutyric acid is successfully screened by screening the single colonies, primary screening by the thin-layer chromatography, and re-screening by the high-performance liquid chromatography. The strain has an extremely high yield of γ-aminobutyric acid which can at least reach 2.53 g/L and can be applied to the preparation of the related dairy product so that the product can be rich in a variety of nutrients such as γ-aminobutyric acid, good in taste, and unique in flavor and has flora balance regulation, anti-anxiety, and anti-aging effects. The strain provides the corresponding idea and inspiration for the development of functional fermented dairy products and has an extremely high application value.

(2) The γ-aminobutyric acid-producing *Streptococcus thermophilus* in the present application is screened and isolated from a traditional fermented dairy product and has high safety, and the screening method is easy to operate and has a high success rate. The preparation method of a dairy product consumes less time, is energy-saving and environmentally friendly, and requires no complex instruments and severe production conditions, which creates conditions for the batch production of the product.

BRIEF DESCRIPTION OF THE SEVERAL VIEWS OF THE DRAWING(S)

FIG. 1 is a picture (magnification 100×) of a microscopic examination result of morphological identification of a strain in Example 2 of the present application. The strain is named *Streptococcus thermophilus* ST36 and deposited in the China General Microbiological Culture Collection Center (CGMCC) on Sep. 18, 2020, with deposit No. CGMCC NO.20676, where the CGMCC is located at No. 3, NO. 1 West Beichen Road, Chaoyang District, Beijing 100101, China.

DETAILED DESCRIPTION

Figure 1:
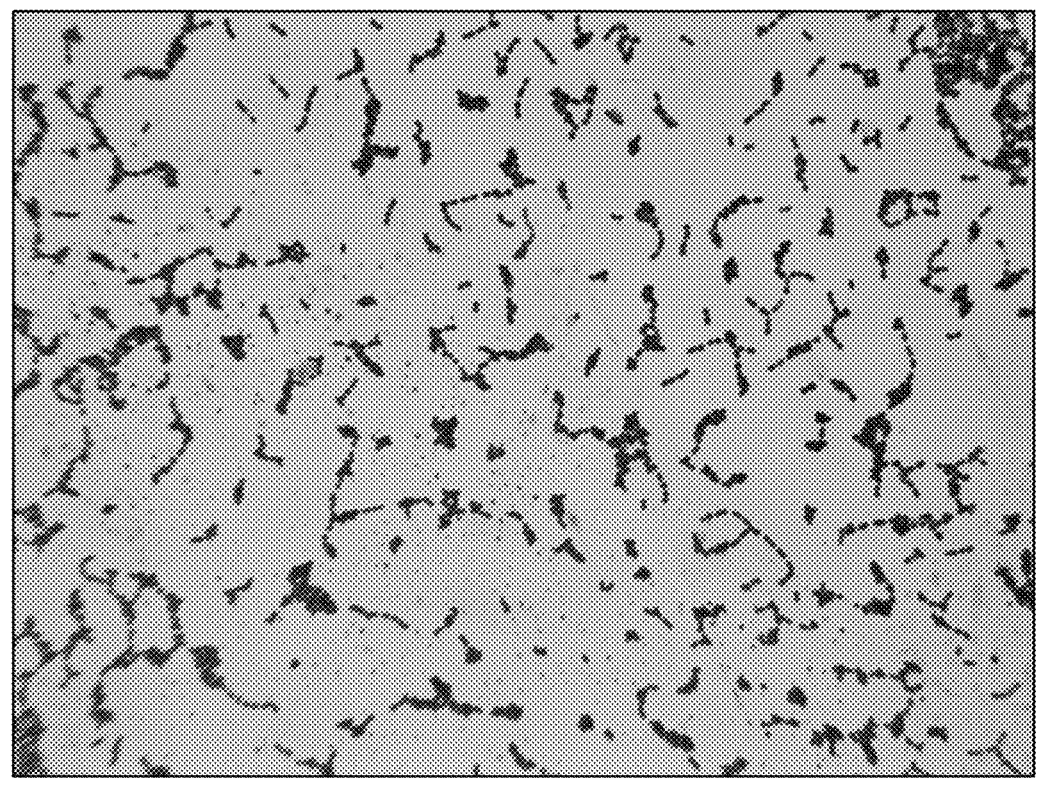

To further elaborate on the technical means adopted and effects achieved in the present application, the present application is described below in conjunction with examples and drawings. It is to be understood that the specific examples set forth below are intended to explain the present application and not to limit the present application.

Experiments without specific techniques or conditions specified in the examples are conducted according to techniques or conditions described in the literature in the art or a product specification. The reagents or instruments used herein without manufacturers specified are conventional products commercially available from proper channels.

Raw Materials:

Milk tofu is fermented milk tofu made by different herdsmen's families in Zhenglan Banner of Xilingol League, Inner Mongolia.

MRS medium was purchased from Hopebio.

Thin-layer chromatography reagents: N-butanol was purchased from Sinopharm Chemical Reagent Co., Ltd, glacial acetic acid was purchased from Sinopharm Chemical Reagent Co., Ltd, and ninhydrin was purchased from Macklin.

High-performance liquid chromatography reagents: Ortho-phthalaldehyde was purchased from Tianjin Guangfu Fine Chemical Research Institute, and γ-aminobutyric acid was purchased from Sigma Corporation.

Gram's dyeing reagent was purchased from Beijing Solarbio Biotechnology Co., Ltd.

General primers were purchased from Sangon Biotech (Shanghai) Co., Ltd.

PCR amplification reagents were purchased from Sangon Biotech (Shanghai) Co., Ltd.

*Lactobacillus bulgaricus* LB42 was from a strain library of Wecare Probiotics (Suzhou) Co., Ltd. The strain is named *Lactobacillus delbrueckii* subsp. *bulgaricus* LB42 and deposited in the China General Microbiological Culture Collection Center (CGMCC) on May 11, 2018, with deposit No. CGMCC NO.15751, where the CGMCC is located at No. 3, NO. 1 West Beichen Road, Chaoyang District, Beijing 100101, China.

*Lactobacillus casei* LC89 was from the strain library of Wecare Probiotics (Suzhou) Co., Ltd. The strain is named *Lactobacillus casei* LC89 and deposited in the China General Microbiological Culture Collection Center (CGMCC) on Mar. 5, 2018, with deposit No. CGMCC NO.15409, where the CGMCC is located at No. 3, NO. 1 West Beichen Road, Chaoyang District, Beijing 100101, China.

Example 1

In this example, a γ-aminobutyric acid-producing strain was screened by the specific steps described below.

(1) A milk tofu sample was diluted with normal saline at gradients of 10-8, 10-9, and 10-10, coated on the surface of an MRS solid medium containing bromocresol purple, and cultured at 37° C. for 60 h and yellow single colonies were screened; the obtained single colonies were repeatedly streaked and cultured three times to obtain pure colonies, and the pure colonies were inoculated in an MRS liquid medium, cultured at 37° C. for 18 h, and then mixed with 40% glycerol and cryopreserved at −80° C.

(2) The cryopreserved bacteria were inoculated in an MRS liquid medium, activated and cultured twice at 37° C. for 18 h, inoculated at an inoculation volume of 2% in an MRS liquid medium containing 1% L-sodium glutamate, statically cultured at 37° C. for 48 h, and centrifuged at 6500 rpm for 5 min to obtain a culture supernatant. The supernatant (2 μL) of a fermentation broth was pipetted with a microsampler, spotted on a chromatographic paper, chromatographed on a chromatographic cylinder, and compared with a standard product of γ-aminobutyric acid and L-sodium glutamate which had a concentration of 1 g/L, and an ability of a strain to produce γ-aminobutyric acid was primarily determined to obtain a primarily screened strain.

(3) The primarily screened strain was activated and cultured in an MRS liquid medium at 37° C. for 16 h, inoculated at an inoculation volume of 2% in an MRS liquid medium containing 1% L-sodium glutamate, statically cultured at 37° C. for 48 h, and centrifuged to obtain a culture fermentation broth, and a content of γ-aminobutyric acid in the fermentation broth was loaded and detected by an ortho-phthalaldehyde (OPA) pre-column derivatization-ultraviolet detection method to obtain a re-screened strain.

After the preceding operations, a strain with a high yield of γ-aminobutyric acid was successfully screened and subjected to morphological identification and 16S rRNA molecular biological identification.

Example 2

In this example, the γ-aminobutyric acid-producing strain screened in Example 1 was subjected to morphological identification and 16S rRNA molecular biological identification by the specific steps described below.

(1) Morphological Identification

The strain preserved at −80° C. was taken out, thawed, streaked directly on an MRS solid medium plate, and cultured at 37° C. for 48 h. Morphological features of colonies such as shape, color, size, transparency, edge, and surface were observed. Single colonies were picked up for Gram staining. After staining, the cells were observed for size and shape with an oil immersion objective (100×) of a Motic Digital Biological microscope, photographed, and recorded. The result is shown in FIG. 1.

As can be seen from observation, the colonies of the screened strain on the MRS medium were small, round, milky white and surface smooth in morphology. As can be seen from the figure, the strain under microscope is in the shape of a curved short chain with spherical connection, different in length, and Gram-positive.

(2) 16S rRNA Molecular Biological Identification

The strain preserved at −80° C. was taken out, inoculated in an MRS liquid medium, and cultured at 37° C. for 18 h. A bacteria liquid (1 mL) was pipetted to a centrifuge tube and centrifuged at 12000 rpm for 5 min. The supernatant was removed and the strains were collected. The strains were mixed with sterile water, added with a general primer for bacteria, and subjected to PCR amplification, and the amplification product was sequenced and identified.

As can be seen from sequencing, the 16S rDNA sequence of the strain has a length of 1484 bp. The sequence is as shown in SEQ ID No. 1.

```
SEQ ID No. 1:
GCTCAGGACGAACGCTGGCGGCGTGCCTAATACATGCAAGTAGAACGCT

GAAGAGAGGAGCTTGCTCTTCTTGGATGAGTTGCGAACGGGTGAGTAAC

GCGTAGGTAACCTGCCTTGTAGCGGGGGATAACTATTGGAAACGATAGC

TAATACCGCATAACAATGGATGACACATGTCATTTATTTGAAAGGGGCA

ATTGCTCCACTACAAGATGGACCTGCGTTGTATTAGCTAGTAGGTGAGG

TAATGGCTCACCTAGGCGACGATACATAGCCGACCTGAGAGGGTGATCG

GCCACACTGGGACTGAGACACGGCCCAGACTCCTACGGGAGGCAGCAGT

AGGGAATCTTCGGCAATGGGGGCAACCCTGACCGAGCAACGCCGCGTGA

GTGAAGAAGGTTTTCGGATCGTAAAGCTCTGTTGTAAGTCAAGAACGGG

TGTGAGAGTGGAAAGTTCACACTGTGACGGTAGCTTACCAGAAAGGGAC

GGCTAACTACGTGCCAGCAGCCGCGGTAATACGTAGGTCCCGAGCGTTG

TCCGGATTTATTGGGCGTAAAGCGAGCGCAGGCGGTTTGATAAGTCTGA

AGTTAAAGGCTGTGGCTCAACCATAGTTCGCTTTGGAAACTGTCAAACT

TGAGTGCAGAAGGGGAGAGTGGAATTCCATGTGTAGCGGTGAAATGCGT

AGATATATGGAGGAACACCGGTGGCGAAAGCGGCTCTCTGGTCTGTAAC

TGACGCTGAGGCTCGAAAGCGTGGGGAGCGAACAGGATTAGATACCCTG

GTAGTCCACGCCGTAAACGATGAGTGCTAGGTGTTGGATCCTTTCCGGG

ATTCAGTGCCGCAGCTAACGCATTAAGCACTCCGCCTGGGGAGTACGAC

CGCAAGGTTGAAACTCAAAGGAATTGACGGGGGCCCGCACAAGCGGTGG

AGCATGTGGTTTAATTCGAAGCAACGCGAAGAACCTTACCAGGTCTTGA

CATCCCGATGCTATTTCTAGAGATAGAAAGTTACTTCGGTACATCGGTG

ACAGGTGGTGCATGGTTGTCGTCAGCTCGTGTCGTGAGATGTTGGGTTA

AGTCCCGCAACGAGCGCAACCCCTATTGTTAGTTGCCATCATTCAGTTG

GGCACTCTAGCGAGACTGCCGGTAATAAACCGGAGGAAGGTGGGGATGA

CGTCAAATCATCATGCCCCTTATGACCTGGGCTACACACGTGCTACAAT

GGTTGGTACAACGAGTTGCGAGTCGGTGACGGCGAGCTAATCTCTTAAA

GCCAATCTCAGTTCGGATTGTAGGCTGCAACTCGCCTACATGAAGTCGG

AATCGCTAGTAATCGCGGATCAGCACGCCGCGGTGAATACGTTCCCGGG

CCTTGTACACACCGCCCGTCACACCACGAGAGTTTGTAACACCCGAAGT

CGGTGAGGTAACCTTTTGGAGCCAGCCGCCTAAGGTGGGACAGATGATT

GGGGTGAAGTCGTA.
```

Example 3

Based on the morphological identification and 16S rRNA molecular biological identification results in Example 2, it was confirmed that the strain belonged to *Streptococcus thermophilus* and was named *Streptococcus thermophilus* ST36. *Streptococcus thermophilus* ST36 was deposited in the China General Microbiological Culture Collection Center on Sep. 18, 2020, with deposit No. CGMCC NO.20676, where the CGMCC is located at No. 3, NO. 1 West Beichen Road, Chaoyang District, Beijing 100101, China.

Example 4

In this example, the γ-aminobutyric acid-producing strain screened in Example 1 was used for preparing functional yogurt rich in γ-aminobutyric acid. Specific steps were described below.

(1) *Streptococcus thermophilus* ST36 producing γ-aminobutyric acid and *Lactobacillus bulgaricus* LB42 were inoculated in an MRS liquid medium separately and cultured at 42° C. for 16 h to activate the strain.

(2) 12% skim milk powder was configured, dispensed into clean tubes, and sterilized at 115° C. for 15 min to obtain a skim milk medium. The activated *Streptococcus thermophilus, Lactobacillus bulgaricus*, and *Lactobacillus casei* were each inoculated at an inoculation volume of 3% in the skim milk medium and cultured at 42° C. for 16 h to obtain the fermentation agents of the corresponding strains.

(3) 1.2% light cream, 89.2% raw milk, 0.5% stabilizer, 8% white sugar, 0.5% whey protein powder, and 0.3% sodium glutamate were mixed at 70° C., hydrated at 40° C. for 30 min, homogenized at 70° C. under 20 MPa, pasteurized at 85° C. for 20 min, and cooled by circulating water to 45° C. to obtain a fermentation base.

(4) The fermentation agents were inoculated in the fermentation base, fermented at 42° C. for 24 h, cooled to 4° C., and post-matured to obtain the functional yogurt rich in γ-aminobutyric acid, where the inoculation volume of the fermentation agent of *Streptococcus thermophilus* was 6%, and the inoculation volume of the fermentation agent of *Lactobacillus bulgaricus* was 2%.

Example 5

In this example, the γ-aminobutyric acid-producing strain screened in Example 1 was used for preparing a lactic acid bacteria beverage rich in γ-aminobutyric acid. Specific steps were described below.

(1) *Streptococcus thermophilus* ST36 producing γ-aminobutyric acid, *Lactobacillus bulgaricus* LB42, and *Lactobacillus casei* LC89 were inoculated in an MRS liquid medium separately and cultured at 37° C. for 16 h to activate the strain.

(2) 12% skim milk powder was configured, dispensed into clean tubes, and sterilized at 115° C. for 15 min to obtain a skim milk medium. The activated *Streptococcus thermophilus, Lactobacillus bulgaricus*, and *Lactobacillus casei* were each inoculated at an inoculation volume of 3% in the skim milk medium and cultured at 37° C. for 16 h to obtain the fermentation agents of the corresponding strains.

(3) 16.3% whole milk powder, 6% white sugar, 0.7% sodium glutamate, and water were mixed at 55° C., hydrated at 45° C. for 30 min, homogenized at 65° C. under 15 MPa, pasteurized at 90° C. for 15 min, and cooled by circulating water to 40° C. to obtain a fermentation base.

(4) The fermentation agents were inoculated in the fermentation base, fermented at 37° C. for 48 h, cooled to 4° C., and post-matured to obtain the fermentation product, where the inoculation volume of the fermentation agent of *Streptococcus thermophilus* was 6%, the inoculation volume of the fermentation agent of *Lactobacillus bulgaricus* was 3%, and the inoculation volume of the fermentation agent of *Lactobacillus casei* was 1.5%.

(5) A thickening agent and white sugar were mixed at a mass ratio of 1:5, where a mass ratio of pectin to soy polysaccharide in the thickening agent was 3:2, the mixture was added with water and stirred until a final concentration of pectin was 0.3% and a final concentration of soy polysaccharide was 0.2%, and the remaining white sugar was added. The mixture was placed still and cooled to 20° C., added with 18.3% fermentation product to a volume, added with citric acid to adjust the acid to 60° T, homogenized at 65° C. under 15 MPa, sterilized at 85° C. for 20 min, and cooled to 25° C. to obtain the lactic acid bacteria beverage rich in γ-aminobutyric acid.

Example 6

In this example, the γ-aminobutyric acid-producing strain screened in Example 1 was used for preparing a brown lactic acid bacteria beverage rich in γ-aminobutyric acid. Specific steps were described below.

(1) *Streptococcus thermophilus* ST36 producing γ-aminobutyric acid, *Lactobacillus bulgaricus* LB42, and *Lactobacillus casei* LC89 were inoculated in an MRS liquid medium separately and cultured at 37° C. for 16 h to activate the strain.

(2) 12% skim milk powder was configured, dispensed into clean tubes, and sterilized at 115° C. for 15 min to obtain a skim milk medium. The activated *Streptococcus thermophilus, Lactobacillus bulgaricus*, and *Lactobacillus casei* were each inoculated at an inoculation volume of 3% in the skim milk medium and cultured at 37° C. for 16 h to obtain the fermentation agents of the corresponding strains.

(3) 16.3% whole milk powder, 3.9% white sugar, 3.9% glucose, 0.7% sodium glutamate, and water were mixed at 55° C., hydrated at 50° C. for 15 min, homogenized at 65° C. under 15 MPa, pasteurized at 80° C. for 30 min, subjected to a Maillard reaction at a constant temperature of ° C. for 120 min to become brown, and cooled by circulating water to 40° C. to obtain a fermentation base.

(4) The fermentation agents were inoculated in the fermentation base, fermented at 42° C. for 48 h, cooled to 6° C., and post-matured to obtain the fermentation product, where the inoculation volume of the fermentation agent of *Streptococcus thermophilus* was 6%, the inoculation volume of the fermentation agent of *Lactobacillus bulgaricus* was 6%, and the inoculation volume of the fermentation agent of *Lactobacillus casei* was 2%.

(5) A thickening agent and white sugar were mixed at a mass ratio of 1:5, where a mass ratio of pectin to soy polysaccharide in the thickening agent was 3:2, the mixture was added with water and stirred until a final concentration of pectin was 0.3% and a final concentration of soy polysaccharide was 0.2%, and the remaining white sugar was added. The mixture was placed still and cooled to 20° C., added with 18.3% fermentation product to a volume, added with citric acid to adjust the acid to 60° T, homogenized at 70° C. under 20 MPa, sterilized at 85° C. for 20 min, and cooled to 25° C. to obtain the lactic acid bacteria beverage rich in γ-aminobutyric acid.

Detection of the Content of γ-Aminobutyric Acid

The content of γ-aminobutyric acid in the γ-aminobutyric acid-containing dairy products prepared in Examples 4 and 5 was detected by the specific steps described below.

(1) Pre-Column Derivatization

A to-be-tested sample was centrifuged at 12000 rpm, and the supernatant (200 μL) was mixed with a derivatization agent (600 μL) for derivatization. The reaction solution was filtered through a 0.22 μm microporous cellulose filter membrane and immediately loaded for detection.

(2) Chromatographic Conditions

Chromatographic column: Luna-C18 column (250×4.6 mm, 5 μm); flowrate: 0.8 mL/min; column temperature: 30° C.; detection wavelength: 334 nm; injection manner: manual injection; injection volume: 5 μL.

(3) Standard Curve Making

The standard of γ-aminobutyric acid was prepared into solutions with concentrations of 0.1 g/L, g/L, 1 g/L, 2 g/L, and 3 g/L, separately. The solutions were derivatized, injected, and determined. The standard curves were made with the concentration of γ-aminobutyric acid as an abscissa and peak areas corresponding to different concentrations as an ordinate.

Figure 2:
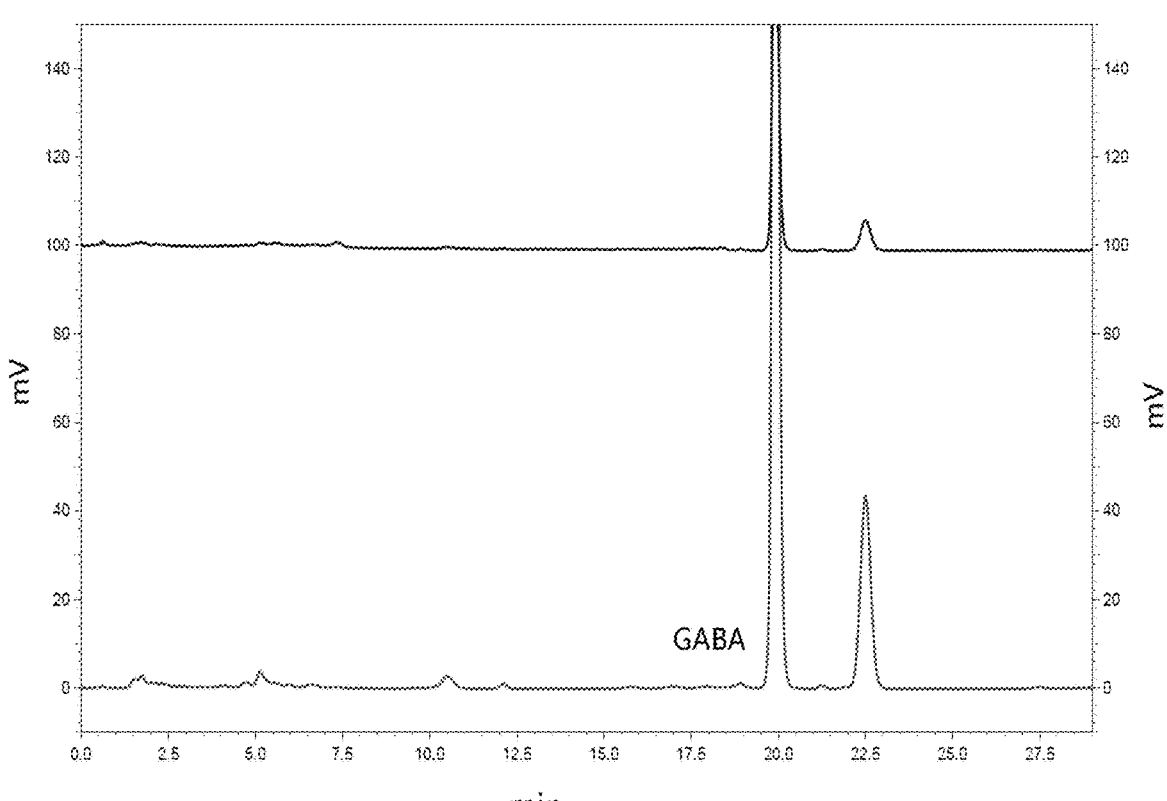
FIG. 2 is a picture of a high-performance liquid chromatography result of functional yogurt prepared in Example 4 of the present application.
Figure 3:
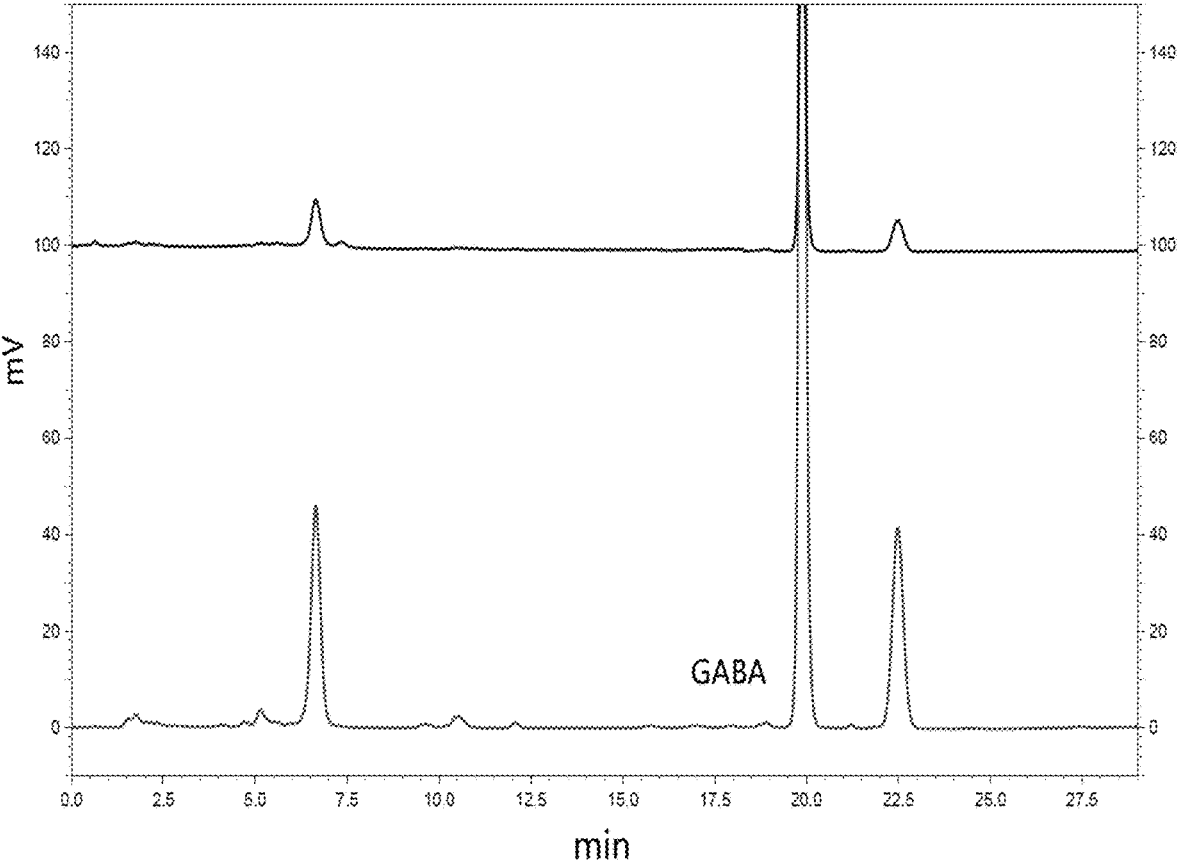
FIG. 3 is a picture of a high-performance liquid chromatography result of a lactic acid bacteria beverage prepared in Example 5 of the present application.

The results of detection of the content of γ-aminobutyric acid in the dairy products prepared in Examples 4 and 5 are shown in FIGS. 2 and 3.

As can be seen from the figure, FIG. 2 is a picture of a high-performance liquid chromatography result of the functional yogurt prepared in Example 4, and with a peak of the standard at 19.907 min as a determination criterion, the sample in Example 4 has a peak with a very large peak area at 19.907 min, indicating that the to-be-tested sample contains γ-aminobutyric acid and the content of γ-aminobutyric acid is measured to be 3.03 g/L; FIG. 3 is a picture of a high-performance liquid chromatography result of the lactic acid bacteria beverage prepared in Example 5, and the result shows that the sample contains γ-aminobutyric acid and the content of γ-aminobutyric acid is measured to be 2.53 g/L. The above results show that the fermented milk product prepared using γ-aminobutyric acid-producing *Streptococcus thermophilus* contains γ-aminobutyric acid whose content can at least reach 2.53 g/L.

To sum up, a strain of γ-aminobutyric acid-producing *Streptococcus thermophilus* is screened in the present application, the strain has a strong γ-aminobutyric acid synthesis ability and a short fermentation period and is applied to the preparation of the related dairy product, and the product is rich in γ-aminobutyric acid, can regulate an intestinal flora balance, relieve pressure, and improve sleep, is beneficial for physical and mental health, good in taste, and unique in flavor, and has a good eating feeling; and the preparation method is simple, efficient, energy-saving, and environmentally friendly and has a wide application prospect in practical processing and production.

The applicant has stated that although the detailed method of the present application is described through the examples described above, the present application is not limited to the detailed method described above, which means that the implementation of the present application does not necessarily depend on the detailed method described above. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

What is claimed is:

1. A preparation method of a γ-aminobutyric acid-containing dairy product, comprising:

(a) activating a γ-aminobutyric acid-producing *Streptococcus thermophilus* strain: inoculating γ-aminobutyric acid-producing *Streptococcus thermophilus* in a de Man, Rogosa, Sharpe (MRS) liquid medium and culturing the γ-aminobutyric acid-producing *Streptococcus thermophilus* strain at 37° C. to 45° C. for 12-24 h;

(b) preparing a fermentation agent: inoculating and culturing the γ-aminobutyric acid-producing *Streptococcus thermophilus* strain after activating in a sterilization skim milk medium to obtain the fermentation agent; wherein the inoculating is conducted at a volume of 2%-5%; and a mass fraction of skim milk powder in the skim milk medium is 10%-15%;

(c) preparing a fermentation base: mixing raw materials, hydration, homogenization, and sterilization to obtain the fermentation base; wherein a raw material of the fermentation base comprises any one of raw milk, whole milk powder, white sugar, sodium glutamate, glucose, light cream, a stabilizer, whey protein powder, or a thickening agent or a combination of at least two selected therefrom; and (d) conducting inoculation and fermentation: inoculating the fermentation agent to the fermentation base, and conducting inoculation and fermentation at 37° C. to 43° C. for 24-48 h; wherein an inoculation volume of the fermentation agent during the inoculation and fermentation is 1.58-6%;

wherein the γ-Aminobutyric acid-producing *Streptococcus thermophilus* is named *Streptococcus thermophilus* ST36 and deposited in the China General Microbiological Culture Collection Center on Sep. 18, 2020, with deposit No. CGMCC NO.20676; and wherein a 16S rDNA sequence of the γ-Aminobutyric acid-producing *Streptococcus thermophilus* is as shown in SEQ ID No.

2. The preparation method of a γ-aminobutyric acid-containing dairy product according to claim 1, comprising the following steps:

(1) inoculating strains of γ-aminobutyric acid-producing *Streptococcus thermophilus* and *Lactobacillus bulgaricus* and/or *Lactobacillus casei* in an MRS liquid medium separately and culturing the strains of γ-aminobutyric acid-producing *Streptococcus thermophilus* and *Lactobacillus bulgaricus* and/or *Lactobacillus casei* after inoculating at 37° C. to 45° C. for 12-24 h for activating;

(2) inoculating the strains of γ-aminobutyric acid-producing *Streptococcus thermophilus* and *Lactobacillus bulgaricus* and/or *Lactobacillus casei* after activating at an inoculation volume of 28-5% in a skim milk medium having a mass fraction of 10%-15% and sterilized at 110° C. to 120° C. for 10-20 min and culturing the strains of γ-aminobutyric acid-producing *Streptococcus thermophilus* and *Lactobacillus bulgaricus* and/or *Lactobacillus casei* after activating at 37° C. to 43° C. for 16-24 h to obtain a fermentation agent;

(3) mixing raw materials of a fermentation base, conducting hydration at 40° C. to 50° C. for 20-40 min, conducting homogenization at 60° C. to 70° C. under 10-20 MPa, conducting pasteurization at 80° C. to 90° C. for 15-30 min, and cooling by circulating water to 40° C. to 45° C. to obtain the fermentation base;

(4) inoculating the fermentation agent to the fermentation base at a volume of 1.58-6%, conducting inoculation and fermentation at 37° C. to 43° C. for 24-48 h, cooling to 0° C. to 6° C., and conducting post-maturation to obtain a fermentation product;

(5) formulating a thickening agent and white sugar with a mass ratio of 1:(20-25) at 60° C. to 75° C., cooling to 20° C. to 30° C., adding the fermentation product, then determining a constant volume, adjusting an acid condition, homogenizing, and sterilizing to obtain the γ-aminobutyric acid-containing dairy product.

3. The preparation method of a γ-aminobutyric acid-containing dairy product according to claim 1;

wherein the γ-aminobutyric acid-containing dairy product comprises any one of fermented milk, a lactic acid bacteria beverage, or a brown lactic acid bacteria beverage.

4. The preparation method of a γ-aminobutyric acid-containing dairy product according to claim 1, wherein activating a strain further comprises a step of inoculating *Lactobacillus bulgaricus* and/or *Lactobacillus casei* in an MRS liquid medium separately.

5. The preparation method of a γ-aminobutyric acid-containing dairy product according to claim 1, wherein the sterilization is conducted at a temperature of 110° C. to 120° C. for 10-20 min;

a mass fraction of skim milk powder in the skim milk medium is 12%; and the culturing is conducted at a temperature of 37° C. to 43° C. for 16-24 h.

6. The preparation method of a γ-aminobutyric acid-containing dairy product according to claim 1, wherein the hydration is conducted at a temperature of 40° C. to 50° C. for 20-40 min;

the homogenization is conducted at a temperature of 60° C. to 70° C. under a pressure of 10-20 MPa;

the sterilization is conducted by pasteurization, wherein the pasteurization is conducted at a temperature of 80° C. to 90° C. for 15-30 min;

the sterilization is followed by a step of cooling to 40° C. to 45° C.;

the cooling comprises cooling by circulating water.

7. The preparation method of a γ-aminobutyric acid-containing dairy product according to claim 1, wherein the inoculation and fermentation further comprises a step of cooling to 0° C. to 6° C.; and a step of post-maturation is further included after the cooling.

8. The preparation method of a γ-aminobutyric acid-containing dairy product according to claim 1, wherein the preparation method further comprises a step of secondary dosing;

the secondary dosing comprises steps of formulating a solvent, adding a fermentation product, then determining a constant volume, adjusting an acid condition, homogenizing, and sterilizing.

9. The preparation method of a γ-aminobutyric acid-containing dairy product according to claim 8, wherein the solvent comprises a thickening agent, white sugar, and water;

the thickening agent comprises pectin and/or soy polysaccharide;

a mass ratio of the thickening agent to white sugar is 1:(20-25).

10. The preparation method of a γ-aminobutyric acid-containing dairy product according to claim 8, wherein the solvent is formulated at 60° C. to 75° C.;

the fermentation product is added at a temperature of 20° C. to 30° C.

* * * * *